Figure 7:
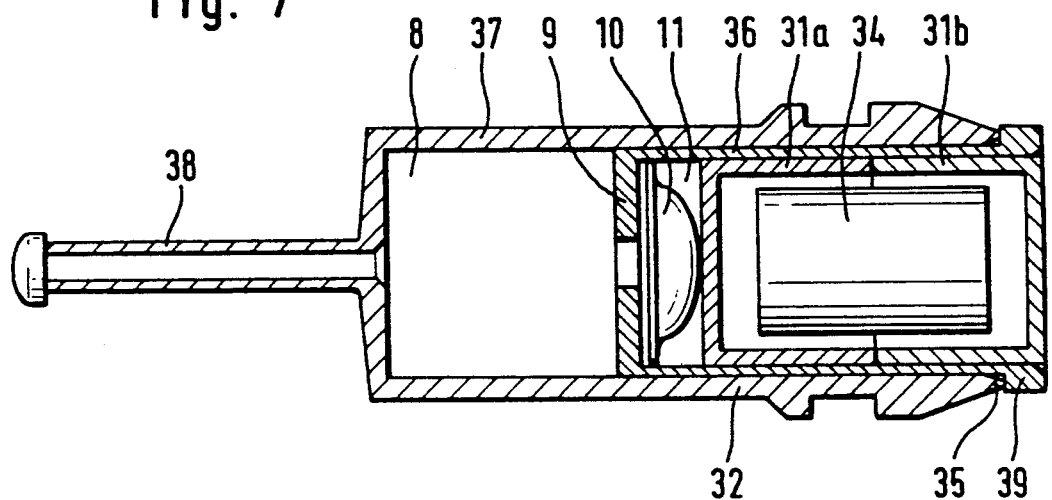

United States Patent [19]

Mühlbauer

[11] Patent Number: 5,088,830
[45] Date of Patent: Feb. 18, 1992

[54] ARRANGEMENT FOR OPERATING A MULTI-COMPONENT MIXING CAPSULE, IN PARTICULAR FOR DENTAL PURPOSES, BY MEANS OF A VIBRATORY MIXING DEVICE

[75] Inventor: Ernst Mühlbauer, Elbgaustrasse 248, 2000 Hamburg 53, Fed. Rep. of Germany

[73] Assignee: Ernst Mühlbauer, Hamburg, Fed. Rep. of Germany

[21] Appl. No.: 402,826

[22] Filed: Sep. 5, 1989

[30] Foreign Application Priority Data

Sep. 27, 1988 [DE] Fed. Rep. of Germany ....... 3832757

[51] Int. Cl.⁵ .............................................. B01F 11/00
[52] U.S. Cl. .................................. 366/108; 366/210; 366/602
[58] Field of Search ............... 366/602, 108, 212, 209, 366/210, 215, 216, 239, 240, 237, 110, 111, 112

[56] References Cited

U.S. PATENT DOCUMENTS

| | | | |
|---|---|---|---|
| 2,487,236 | 11/1949 | Greenberg | 366/602 |
| 3,638,918 | 2/1972 | Denholtz | 366/602 |
| 3,815,115 | 6/1974 | Inque | 366/602 |
| 4,136,775 | 1/1979 | Zaltsman | 366/602 |
| 4,182,447 | 1/1980 | Kay | 366/602 |
| 4,818,115 | 4/1989 | Tornqvist | 366/212 |
| 4,871,261 | 10/1989 | Randklev | 366/602 |

*Primary Examiner*—Robert W. Jenkins
*Attorney, Agent, or Firm*—Chilton, Alix & Van Kirk

[57] ABSTRACT

Arrangement for operating a multi-component mixing capsule, in particular for dental purposes, by means of a vibratory mixing device, to activate the capsule and to mix the contents of the capsule. The mixing capsule contains a mixing space and a chamber to receive a foil sachet containing a liquid component. The chamber is delimited by two walls, one of which can be moved towards the other to activate the capsule, that is to empty the foil sachet in the mixing space. This takes place according to the invention by means of a first striking body, which as a result of mixing vibration is accelerated against the chamber wall.

20 Claims, 2 Drawing Sheets

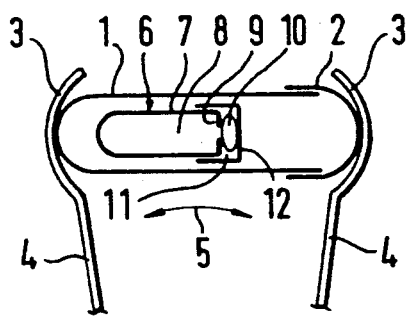
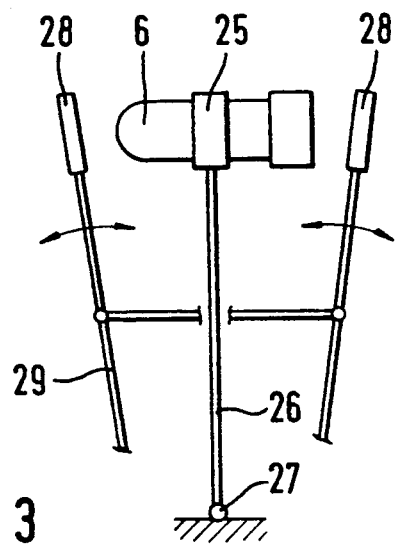
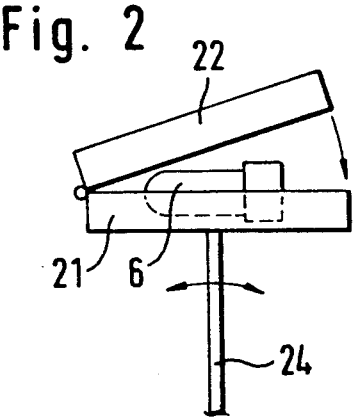
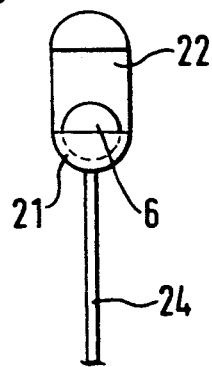
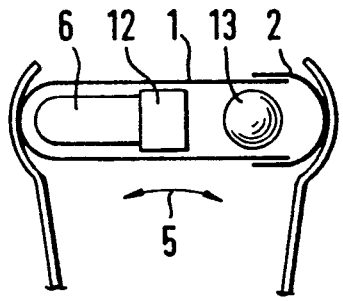
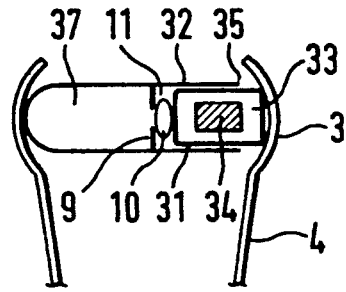

ARRANGEMENT FOR OPERATING A MULTI-COMPONENT MIXING CAPSULE, IN PARTICULAR FOR DENTAL PURPOSES, BY MEANS OF A VIBRATORY MIXING DEVICE

The invention relates to an arrangement for operating a multi-component mixing capsule, in particular for dental purposes, by means of a vibratory mixing device, in which arrangement the mixing capsule comprises a mixing space and a chamber, which is separated from the latter by means of a bursting closure, is to receive a liquid component and is delimited by a first wall, which is rigidly connected to the container part which forms the mixing space, and a second wall, which can be moved towards the first wall under the effect of an activation force in order to open the bursting closure and to displace the liquid component from the chamber.

In a known type of mixing capsules for dental purposes (DE-AS 12 87 251; DE-PS 24 00 970; DE-PS 19 39 316), the long mixing space is separated from the chamber by a perforated wall, which delimits the chamber on the one side. On the other side, it is delimited by a closing lid, which is telescopically displaceable towards the capsule part which forms the mixing space, or a piston. In order to activate the capsule, that is to burst a foil sachet containing the liquid component, such high forces are exerted on the lid or the piston respectively by means of a special tool, that the foil sachet bursts in the area of an opening in the separating wall and discharges its contents into the mixing space. The foil sachet bears against the movable chamber wall with an area, of which the size is a multiple of the cross-sectional area of the opening. A hydraulic force transfer thus takes place, with the result that the force which is necessary to displace the movable wall is many times greater than the force which would be necessary to rupture the sachet in the area of the opening. The forces which are to be exerted on the movable wall are consequently considerable and amount to several decanewton. It has been considered to reduce this force expenditure by using switchable valve members between the chamber and the mixing space (U.S. Pat. No. 2,527,991). It has not, however, been possible to introduce these in practice, because sufficiently precise valve members cannot be economically manufactured under conditions of mass production.

Mixing capsules for dental purposes are also known (DE-PS 28 31 005), which are activated solely by the mixing motion without special activation action, a foil sachet contained within the mixing space being ruptured and emptied by the forces of inertia which are effective during the mixing vibration. However, this principle cannot be used without further measures with specifically light liquids. This type of capsule can also not be used as an application syringe (DE-PS 19 39 316), because the remains of the sachet which are contained within the mixing space hinder the emptying of the mixing space through a nozzle.

Finally, a dental capsule is known (DE-OS 29 31 262), in which the liquid component is contained in the chamber without an enclosing foil sachet, the separating wall between mixing space and chamber being displaceable in such a manner under the impact force of a pestle contained within the mixing space, that valve openings between chamber and mixing space are opened and the liquid is displaced out of the chamber through these openings into the mixing space. This is possible because the force necessary to displace the wall is small. Even small forces can effect a small displacement of the separating wall, the total displacement being brought about by a large number of repeated, small individual displacements. The capsule has the disadvantage, however, that it is costly to manufacture, because the fit of the displaceable wall in the capsule must satisfy high requirements of tightness. This capsule too cannot be executed in the form of an application syringe, because the pestle in the mixing space hinders the contents of the mixing space from being completely emptied by means of a piston.

The object of the invention is, therefore, to render easier the operatability of the dental capsule indicated in the introduction, which presupposes the presence of a bursting closure, in particular of a foil sachet containing the liquid component. Additionally, the capsule should be suitable for various forms of use, including the execution as an application syringe.

The solution according to the invention consists in the fact that, on the side of the chamber facing away from the mixing space, a guide is provided which runs approximately in the direction of vibration of the mixing device, in which guide a face end of a first striking body faces the second wall of the chamber, is movable in relation to it, is assigned to it by the guide and interacts with it, and that a second striking body is connected to the part of the capsule forming the mixing space, one of the two bodies being connected to the vibration drive of the vibratory mixing device and the other being movable in relation to the latter by means of the guide.

The invention comprises two steps. The first consists in the use of the per se known striking body on the opening of the bursting closure. The second relates to the constructive development.

The first step is surprising in so far as—as described above—high forces are required for the bursting of a foil sachet. It had to be expected that this would demand so large a striking body mass, that the bursting pressure of the foil sachet can be exceeded with one single blow. Such a mass would be so large, that it could not be accommodated in the limited area of a mixing capsule and could not be moved by the limited drive forces of commercial vibratory mixing devices. However, it emerged surprisingly that it is not necessary for the mass to be so large. Even if the force of the individual blow is considerably smaller than the statically effective force, which makes the sachet burst, the opening of the sachet can be achieved by multiple, rapid blow repetition. It emerged that the opening and emptying of the foil sachet takes place in a time span of one to several seconds, which corresponds to a number of blows of a magnitude of 100. From this it must be concluded that fatigue or vibration phenomena play a role in the opening of the sachet, having the effect that, even with a small striking body mass and correspondingly low forces of inertia, the opening of the sachet is completed with reliability.

The second step consists in the constructive development, namely in the arrangement of a striking body outside the mixing space exclusively for the purpose of activating the capsule. The mixing space thus remains free of foreign bodies and can be used as the squirting cylinder of an application capsule.

Since in the first instance a bursting closure is to be understood as a foil sachet, which is made to burst in the area of an opening of a wall separating the mixing space and the chamber, reference is only made to a foil sachet in the following. However, other executions of the bursting closure are also conceivable, for example in the form of a burst foil sealed over the opening or a membrane which is formed integrally with the wall and which can contain predetermined breaking lines. The liquid component is then contained freely within the chamber, the second chamber wall being executed so as to close tightly.

In a preferred embodiment of the invention, the capsule is freely movable in the guide and the first striking body is connected to the vibration drive, the guide and at least a part of the first striking body being advantageously formed by a guide container which receives the capsule, which guide container can preferably be clamped as such into the vibratory mixing device or forms a part of the vibratory mixing device. The second striking body can then be formed by the capsule part which forms the mixing space or be rigidly connected to it. The capsule is thrown backwards and forwards in the guide container between the ends of the latter, the second, movable wall of the chamber impacting against the face wall, which faces it, of the guide container, the activation force acting upon the chamber being defined by the difference in speed and the smaller of the striking body masses involved.

In another advantageous embodiment, the guide is formed by a capsule holder connected to a vibration drive, in which holder the first striking body is freely movable in the vibration direction, the second striking body being formed by the capsule holder. The capsule part forming the mixing space can in this case be rigidly connected to the capsule holder, only the first striking body moving in the free space adjoining the movable chamber wall. In another embodiment, the capsule can also be movable in the capsule holder in the vibration direction, so that both the capsule and the first striking body move freely in the capsule holder. The activation forces are then exerted by the striking body on the movable chamber wall, when the capsule bears against the face end of the capsule holder with its end which faces away from the first striking body and the first striking body impacts against the movable chamber wall. At this decisive moment, the capsule is rigidly connected by contact to the second striking body, so that it can be supported thereon during the impact of the first striking body. It does not matter, whether in addition further collisions occur between the first striking body and the capsule, if the latter is not supported.

In yet another embodiment, the guide can be arranged securely on the capsule, the first striking body being movable therein, while the second striking body is formed by the capsule part forming the mixing space and if applicable by parts of the vibration drive connected rigidly thereto. The rigid connection of the guide to the capsule can then be so designed that the guide constantly forms a part of the capsule and the capsule as such already contains all the elements which make possible automatic activation. This embodiment is advantageous because the capsule can be clamped without further measures into the vibratory mixing device and the activation and mixing take place without assistance. Instead of this it is also possible, however, to connect the multi-use guide with the striking body to the disposable capsule only when the activation and mixing are to take place.

Instead of a striking body which is freely movable in a guide, a striking body which is connected to the capsule, preferably in constant contact with the movable wall or held on the foil sachet, can also be used.

If the striking body is arranged in or on the capsule and the latter is provided with an application nozzle, through which the mixed mass can be directly applied, the guide of the striking body or striking bodies is itself advantageously executed as a piston, through which by means of an application device the feed force can be exerted on the application piston which delimits the mixing chamber. If, in connection with the invention, it is mentioned that the wall separating the mixing space from the chamber is rigidly connected to the capsule part forming the mixing chamber, this does not exclude that this wall, for example as part of such an application piston, is movable in relation to the capsule part forming the mixing space in other functional connections.

The advantage of a freely movable striking body consists in the fact that greater differences in speed between the striking body and the capsule part associated with it can occur, because the capsule part under the influence of the vibration drive can already have carried out a return of motion, while the striking body still continues to move in the previous direction. In order that this is possible, the free movement travel of the striking body in the guide piece holding it should be at least approximately a tenth of the vibration drive amplitude.

In the use of commercial foil sachets and dental mixing devices, the mass of the first striking body can in general be less than 10 grams, preferably even less than 5 grams.

Figure 8:
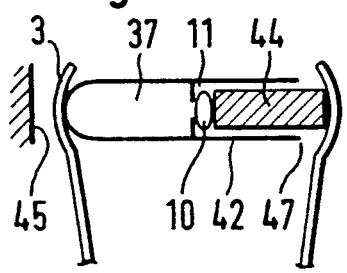
Figure 10:
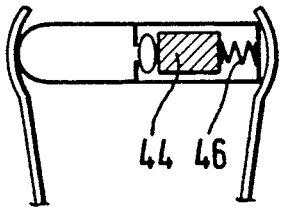
Figure 9:
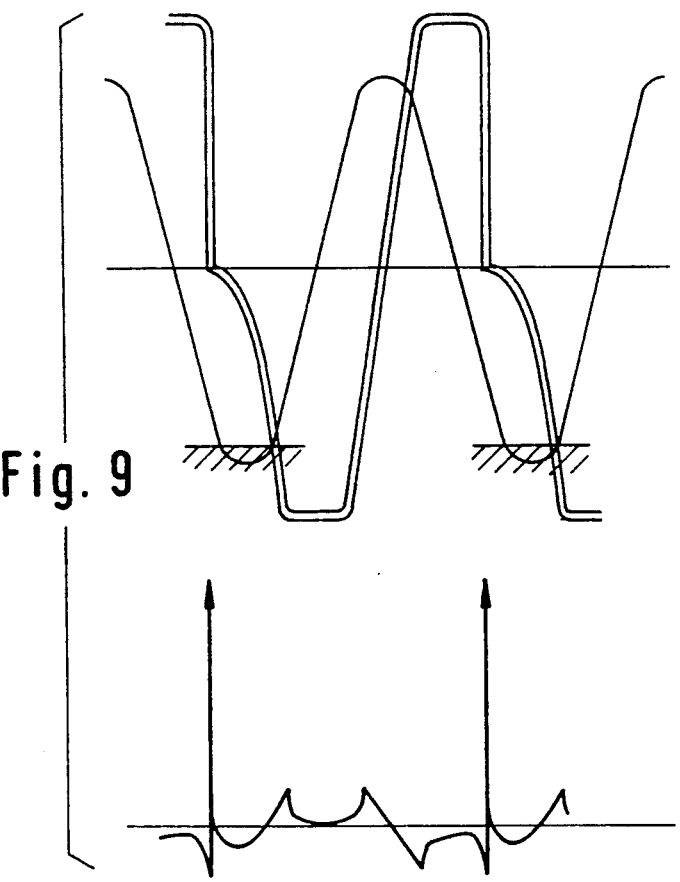

The invention is described below in greater detail with reference to the drawing, which illustrates advantageous exemplary embodiments schematically, and in which FIG. 1 shows a schematic representation of a first embodiment clamped in a vibratory mixing device, FIG. 2 and 3 show a side and front view of a variant of the first embodiment, FIG. 4 shows a further variant of the first embodiment, FIG. 5 shows a representation corresponding to FIG. 1 of a second embodiment, FIG. 6 shows a representation corresponding to FIG. 1 of a third embodiment, FIG. 7 shows a more detailed representation of the third embodiment, FIG. 8 shows a representation corresponding to FIG. 1 of a fourth embodiment, FIG. 9 shows a speed and acceleration diagram of the fourth embodiment and FIG. 10 shows a variant of the fourth embodiment.

In FIG. 1 a long container can be seen which consists of container part 1 and lid 2 and which is clamped between the claws 3 of a commercial vibratory mixing device. As is known, the claws 3 are mounted on arms 4 which are resiliently tensioned towards one another, in order to be able to grip the ends of the long container 1, 2 securely. The vibration is carried out with a frequency of at least 2,500/min, preferably approximately 3,000/min, approximately in the direction of the arrow 5, that is approximately in the longitudinal direction of the container 1, 2.

The container 1, 2 forms a long, cylindrical space to receive and guide the capsule 6. This forms within one part 7 a mixing space 8, which is separated by a perforated wall 9 from a foil sachet 10, which contains the liquid component and which is contained in a chamber 11, which is formed between the perforated wall 9 and a closing lid 12, which can be pushed telescopically onto the capsule part 7 and is held in its respective position by friction The capsule 6 is oblong, as is known from commercial dental capsules, and has in diameter some play in relation to the cylindrical inner space of the container 1, so that it can easily slide therein in a longitudinal direction.

During the mixing vibration, the capsule 6 is thrown backwards and forwards between the face walls, which delimit the inner space of the container 1, 2, whereupon impact forces, which depend upon the difference in speed and the size of the masses involved, act on the lid 12 upon impact against the face wall on the right in the drawing. The difference in speed is defined by the frequency of the vibration drive and the relationship of the free travel of the capsule 6 in the inner space of the container 1, 2 with the vibration amplitude of this container. The free movement travel of the capsule in the container should be less than the vibration amplitude of the container and is preferably smaller than half the vibration amplitude, preferably in the range between a twentieth and a third of this amplitude. This applies also to other embodiments. The masses involved are formed on the one hand by the lid 2 and the parts which at the moment of impact are rigidly connected to it, namely the claw 3 and a part of the associated arm 4. The container 1 can also be added to this mass, if it is rigidly connected to the container 2. These parts together form the first striking body. The second striking body is formed by those parts, which are rigidly connected to the perforated wall 9, that is by the capsule part 7 forming the mixing space 8. The smaller of the two striking body masses is ruling, that is in this example in general the mass of the capsule part 7. It should be at least approximately 3 grams, presupposing a vibration frequency of 3,000/min.

During the mixing vibration the lid 1 of the capsule strikes against the lid 2 of the container 1, 2 so frequently that the foil sachet 10 bursts and discharges its contents through the perforated wall 9 into the mixing space 8, until the liquid component has been completely displaced from the chamber 11.

Capsule 6 and container 1, 2 can be brought onto the market as a simple-to-use unit. Instead of this, it is also possible to treat only the capsule 6 as a one-way unit, while the outer container 1, 2 can be used repeatedly.

Clearly, the container can be changed in many ways in its design and can even lose the character of a container, without losing its functionality. Whereas the embodiment according to FIG. 1 presupposes that the container 1, 2 is a separate part which is to be clamped into the claws 3 of the mixing device, the variant according to FIG. 2 and 3 demonstrates the possibility of designing it as part of the mixing device, in which case it is rigidly connected with a vibration arm 24, which takes the place of the vibration arms 4. The container consists of a first part 21 which is rigidly connected to the vibration arm 24 and a lid part 22, which is removable from the part 21 for the insertion and removal of the capsule 6 and which can be held in the closed position by spring action, a snap closer or similar. The guide does not need to be designed like a container, as the embodiment variant according to FIG. 5 shows.

In the further variant of the first embodiment, which is shown in FIG. 4, the capsule 6 is held by a clamp 25, which is fastened to an arm 26 which is mounted on an articulation in the mixing device at 27. Clamp 25 and arm 26 are designed to be low mass. The capsule is guided in its longitudinal direction by the latter along an arc of a circle around the articulation 27. Instead of an articulation 27, the arm 26 could also be designed as a spring. In the guide path of the capsule 6 there are striking plates 28, the mutual separation of which is slightly longer than the length of the capsule 6. They are fastened on vibration arms 29 which vibrate essentially synchronously and which alternately strike the ends of the capsule 6 and throw the latter backwards and forwards between them. The function is similar to that in the embodiments according to FIG. 1 to 3, the first striking body being formed by the right striking plate and the second striking body by the capsule part forming the mixing space.

The second embodiment according to FIG. 5 differs from that according to FIG. 1 in that, in addition to the capsule 6, there is in the space of the container 1, 2 on the side of the capsule lid 12 a striking body 13 made of specifically heavy material such as metal, which body is for example spherical and has a diameter which is a little smaller than the internal diameter of the outer capsule body 1. The combined length of the capsule 6 and the striking body 13 is less than the length of the inner space of the container 1, 2.

The impact takes place between the ball 13 as the first striking body and the lid 12 of the capsule 6. In general, the capsule is lighter than the striking body 13, so that it is pushed by the latter against the left face wall of the container 1, 2 and is supported there. Thus the first striking body is formed by the ball 13 and the second striking body by the combined masses of the capsule part 7, the container 1 and the left claw 3. As to the rest the function is the same as in the case of the first embodiment.

In the third embodiment according to FIG. 6, the chamber 11 is formed on the one hand by the perforated wall 9 and on the other hand by the face wall of a hollow piston 31, which is guided with weak friction in a rear extension 32 of the container part 37. In the cavity 33 within the hollow piston 31 there is a striking body 34, the length of which is a little shorter than the free length of the cavity 33. Upon every second return of motion, the striking body 34 strikes against the face wall of the hollow piston 31 on the chamber side and presses it against the foil sachet 10, in order to make it burst and to empty it. The function is in this respect similar to that of the first embodiment. In order that the hollow piston 31 remains as constantly as possible in contact with the foil sachet 10, it is advantageously envisaged that the former is pushed to the left in the drawing by an elastic force. This can—as indicated in the drawing—be achieved by the hollow piston 31 extending beyond the rear end 35 of the wall 32, so that it is acted upon by the clamping force of the claw 3.

A preferred exemplary embodiment of the third embodiment is represented in FIG. 7 in detail in longitudinal section and enlarged scale. In it can be seen the capsule part 37, which at the front end supports an application nozzle 38. The perforated wall 9 is designed as the face wall of a piston 36, the rear edge 39 of which grips outwards over the rear edge 35 of the rear wall part 32 of the container part 37. Behind the foil sachet 10, there is inside the piston 36 the hollow piston 31, which is composed of a front half 31a and a rear half 31b, which are not connected to one another and are only held together by weak friction inside the piston 36. They receive the striking body 34, which is approximately 3 mm shorter than the space to receive it in the hollow piston 31.

When the capsule is clamped into a mixing device and the mixing vibration is started, the striking body 34 strikes alternately against the front and the rear face wall of the hollow piston 31. Upon impact against the front face wall which delimits the chamber 11, the body pushes the front hollow piston part 31a against the foil sachet 10 and creates in it a pressure, which after many repeated blows finally leads to the bursting of the latter in the area of the opening in the perforated wall 9. Upon further blows, it pushes the front hollow piston part 31a against the perforated wall 9 until the fluid component has been completely displaced from the foil sachet 10 into the mixing space 8. As the front part 31a of the hollow piston is independent of the rear part 31b, its being pushed forward is not hindered by the tendency of the striking body 34 to push the rear hollow piston part 31b to the right in the drawing or against a stop which is not shown.

During the mixing process, the perforated wall 9 is protected against the forces acting upon it by the contact of the rear edge 39 of the piston 36 against the rear edge 35 of the container part 37 and in this respect rigidly connected to the capsule part 37. When mixing is to be ended and the capsule contents are to be pressed out of the capsule by means of an application device, the hollow piston 31 is pushed forward, as a result of which the rear, projecting edge 39 of the piston 36 loses its inner support and thus no longer provides any resistance to the piston 36 being pushed forward. For a more detailed explanation reference is made to the utility model application G 88 09 184.8.

The embodiment according to FIG. 7 proved itself with the following specifications:

| | |
|---|---|
| Weight of the striking body: | 3 g |
| Travel of the striking body at start of vibration: | 3 mm |
| Travel at end of activation: | 5 mm |
| Start of activation at 2,400/min: | 4-5 sec. |
| Start of activation at 3,000-3,500/min: | approx. 3 sec. |
| Sachet foil: | aluminium soft 0.015 mm. lined with 15 g/m² polypropylene |
| Diameter of opening in perforated wall: | 3 mm |

The fourth embodiment according to FIG. 8 differs from that according to FIG. 6 in that the striking body 44 is not freely movable in the capsule. The activation force is produced by the capsule as a whole being subjected to a high degree of movement which is as blow-like as possible by rapid return of motion. This is indicated in FIG. 8 by the representation on the left next to the claw 3 of a stop 45, against which the claw 3 strikes at the end of each vibration, so that the speed of the capsule is braked in a blow-like manner and this gives rise to high acceleration. In practice, it is generally preferred to initiate the rapid return of motion not by a stop but by means of corresponding execution of the vibration arm drive, for example by suitable execution of the gear which transmits the motor movement to the vibration arms.

It is not necessary, but can be advantageous, to keep the striking body 44, which in this exemplary embodiment also forms one of the walls which delimit the chamber 11, in constant contact with the foil sachet, which takes place in the exemplary embodiment according to FIG. 8 by means of the right claw 3 engaging with the striking body 44 which projects beyond the end 47 of the container wall 42. To this end in the variant according to FIG. 10 a spring 46 is provided inside the capsule.

FIG. 9 shows in the upper part with a thin line the travel and with a double line the speed of the capsule. The travel is cut off at one end of the vibration by the stop 45, so that the speed at this point falls sharply to zero (or in the case of an elastic impact even goes in the opposite direction). Correspondingly, the acceleration diagram below shows a high peak at this point.

We claim:

1. Arrangement for operating a multi-component mixing capsule by means of a vibratory mixing device having a vibration drive, the mixing capsule comprising:
   a mixing space defined by a capsule part and a perforated first wall rigidly formed on the capsule part;
   a chamber proximate the mixing space, the chamber being defined by the first wall, and a second wall which can be moved toward the first wall,
   a bursting closure disposed in the chamber, the closure capable of being opened by movement of the second wall toward the first wall as a result of the operation of said mixing device,
   a guide connected to the mixing device,
   a first striking body disposed outside the mixing space, the first striking body being movable in relation to the first wall of the chamber, and
   a second striking body defined at least in part by the capsule part,
   at least one of the first and second striking bodies being connected to the vibration drive, and either the first or the second striking body being at least partially contained within the guide.

2. Arrangement according to claim 1, characterized in that the mixing capsule (6) is freely movable in the guide (1, 2; 21, 22; 25 to 27) and the first striking body (2; 21, 22; 28) is connected to the vibration drive.

3. Arrangement according to claim 2, characterized in that the guide and at least a part of the first striking body is formed by a guide container (1, 2; 21, 22) which receives the capsule.

4. Arrangement according to claim 3, characterized in that the guide container can be clamped into claws (3) of the vibratory mixing device.

5. Arrangement according to claim 3, characterized in that the guide container (21, 22) is a part of the vibratory mixing device.

6. Arrangement according to claim 2, characterized in that the second striking body (7) comprises the capsule part (7).

7. Arrangement according to claim 1, characterized in that the guide is formed by a capsule holder (1, 2) connected to a vibration drive (4), in which holder the first striking body (13) is freely movable in the vibration direction (5), and that the second striking body is formed by the capsule holder (1, 2).

8. Arrangement according to claim 7, characterized in that the capsule part (7) forming the mixing space (8) is rigidly connected to the capsule holder (1, 2).

9. Arrangement according to claim 7, characterized in that the capsule (6) is freely movable in the vibration direction in the capsule holder (1, 2).

10. Arrangement according to claim 1, characterized in that the guide (31, 42) is arranged securely on the capsule (6) and the first striking body (34, 44) is movable therein, the second striking body being formed by the capsule part (7) forming the mixing space (8).

11. Arrangement according to claim 10, characterized in that the first striking body (34) is freely movable in the guide (31).

12. Arrangement according to claim 11, characterized in that the guide (31) is executed as a piston.

13. Arrangement according to claim 10, characterized in that the second striking body is formed by a portion of the vibration drive.

14. Arrangement according to claim 10, characterized in that the striking body (44) is pushed against the chamber (11) by spring action.

15. Arrangement according to claim 14, characterized in that the striking body (44) is executed as a piston.

16. Arrangement according to claim 14, characterized in that the striking body (44) is executed as a piston.

17. Arrangement according to claim 1, characterized in that the free movement travel of the freely movable striking body (7; 13; 7, 28) in relation to its guide (1, 2; 31; 26 to 29) is at least approximately a tenth of the vibration drive amplitude.

18. Arrangement according to claim 1, characterized in that the mass of the freely movable striking body is smaller than 10 grams.

19. Arrangement according to claim 1, wherein the first striking body has a first end facing the second wall of the chamber, the first end of the first striking body being movable in relation to the second wall of the chamber.

20. Arrangement according to claim 1, wherein the first striking body has a first end forming the second wall of the chamber.

* * * * *

UNITED STATES PATENT AND TRADEMARK OFFICE
CERTIFICATE OF CORRECTION

PATENT NO. : 5,088,830

DATED : February 18, 1992

INVENTOR(S) : Ernst Muhlbauer and Jurgen Engelbrecht

It is certified that error appears in the above-identified patent and that said Letters Patent is hereby corrected as shown below:

On the title page, item [75]

change "Inventor" to -- Inventors -- and insert -- Jurgen Engelbrecht, Petkumstrasse 18, 2000 Hamburg 76, Fed. Rep. of Germany --.

Item [19], after "Mühlbauer" Please add -- et al.--

Signed and Sealed this

Thirteenth Day of July, 1993

Attest:

MICHAEL K. KIRK

Attesting Officer

Acting Commissioner of Patents and Trademarks